United States Patent [19]

Gunther

[11] 4,243,655

[45] Jan. 6, 1981

[54] DENTAL HEALTH-CARE AIDS

[76] Inventor: Roland E. Gunther, R.D. 1, Box 282, New Berlin, N.Y. 13411

[21] Appl. No.: 71,997

[22] Filed: Sep. 4, 1979

Related U.S. Application Data

[63] Continuation-in-part of Ser. No. 960,106, Nov. 13, 1978, abandoned, Ser. No. 960,107, Nov. 13, 1978, abandoned, Ser. No. 960,108, Nov. 13, 1978, abandoned, Ser. No. 960,109, Nov. 13, 1978, abandoned, Ser. No. 960,110, Nov. 13, 1978, abandoned, Ser. No. 960,111, Nov. 13, 1978, abandoned, and Ser. No. 960,112, Nov. 13, 1978, abandoned.

[51] Int. Cl.³ .................. A61K 7/16; A61K 7/26; A61K 31/415; A61K 35/54
[52] U.S. Cl. .................................. 424/19; 424/22; 424/36; 424/48; 424/49; 424/95; 424/177; 424/273 R; 426/3; 426/72; 426/306; 426/311; 426/572; 426/593; 426/631; 426/648; 426/660; 426/659; 426/658
[58] Field of Search .................. 424/19–22, 424/36, 48, 49, 177, 273 R; 426/372, 306, 311, 572, 593, 631, 648, 658–660

[56] References Cited

U.S. PATENT DOCUMENTS

2,370,662  3/1945  Hertz et al. .......................... 424/95

OTHER PUBLICATIONS

Dreizen et al, Intern. Z. Vitamin forsch 33: 321-326 (1963), Effect of Antimetabolites or selected B Vitamins on Experimental Dental Caries in the Rat.

Nevn et al, Chem. Abstr. 52 #14795B (1958) of Nevin et al, J. Dent. Res. 37: 527-531 (1958), Availability of Certain Streptococcal Growth Factors in Human Saliva.

*Primary Examiner*—Shep K. Rose

[57] ABSTRACT

Dental-care Aid Products are formulated to contain Biotin-antagonists. Biotin is an essential nutrient for many microorganisms involved in tooth decay; restricting Biotin availability for the microflora by means of Biotin-antagonists interferes with their ability to develop dental caries.

40 Claims, No Drawings

DENTAL HEALTH-CARE AIDS

This application is a Continuation-in-Part of pending applications Ser. No. 960,106 through 960,112 filed Nov. 13, 1978 now abandoned.

BACKGROUND OF THE INVENTION

1. Field of the Invention

This application relates to Dental-care Aid Products; these incorporate Biotin-antagonists for the purpose of inhibiting the development and effects of caries-producing microorganisms in the human mouth.

2. Description of the Prior Art

No previously used or described products are known to the inventor, of any kind, whose function it is to control the environment in which oral bacteria exist, in such a way as to deprive them of the full use of necessary Vitamins that are normally present in the saliva.

SUMMARY OF THE INVENTION

This invention is based upon the principle of severely limiting the availability of Biotin, which is normally present in human saliva, to those microorganisms in the human mouth, that are the prime causative agents of tooth decay. It has been found that Biotin is an essential nutrient for these microorganisms, and the Biotin-deprivation is intended to severely limit their development, and consequently their ability to create caries. The Biotin-deprivation is brought about by the introduction through various Dentalcare Aid products, of Biotin-antagonists into the human mouth. It is an important and noteworthy feature of the invention that the Biotin-antagonists bring about their effects directly in the miniecosystem that exists in the human mouth; Biotin stores in the body proper are not intended to be affected and in the magnitudes of Biotin-antagonists involved, the possible effects on total body stores of Biotin are insignificant.

DESCRIPTION OF THE PREFERRED EMBODIMENTS

For the purpose of elucidating this invention, some background is first provided on the mechanism of tooth-decay, on the vitamin Biotin, and the requirement of decay-fostering microorganisms for this vitamin, and on Biotin-antagonists that are able to block the normal pathways of Biotin-uptake by the offending microorganisms.

The mechanism whereby dental caries appear to be formed is based on a two-fold effect: first, the accumulation of plaque on the tooth surfaces by the action of one type of microorganisms that produce carbohydrate-based polymers such as dextrans. Secondly, there is the production of acids, usually by another group of microorganisms, and these are the cause of the actual breakdown in the integrity of the tooth structure.

The acid-formers inhabit the plaque; in addition to providing a sheltered environment for these bacteria, the plaque can also provide them with nutrients. Also, the plaque can hold the acids that are produced in close proximity to the tooth-surfaces, so that the acids are less likely to become diluted, or even washed away from the tooth surfaces by other liquids in the mouth.

Plaque is based mainly on sucrose polymers, and the microorganism most strongly suspected of being responsible for its formation is Streptococcus mutans. This was reported by J. K. Clark in 1924 (Brit. Jour. Exp. Path. 5:141–147). The monumental work on this subject has been done more recently by J. Carlsson (Odont Revy 18: 55–74 (1967), Ibid 19:137–160 (1968), Ibid 19: Suppl. 14 (1968)). In 1970 Carlsson sought to establish nutrient needs for Streptococcus mutans. Using a strain designated as JC2, which was isolated from humans, he found Biotin to be essential for growth (Caries Research 4:305–320 (1970)).

The acid-producing microorganisms have similar requirements: In 1944 Niven (Jour. Bact. 47:343–350) showed that of 21 strains of Streptococcus lactis examined for vitamin requirements, all needed Biotin for growth. In 1950 S. A. Koser and H. J. Fisher isolated 26 strains of Lactobacilli from human saliva and found that Biotin was essential for growth for all of them (J. Dental Res. 29:760–773).

While Lactic Acid seems to be considered to be the acid most responsible for tooth decay (A. T. Brown in Present Knowledge of Nutrition, 1976, by the Nutrition Foundation, p. 492) "particiating in the deminerilization of enamel and cementum in coronal and root surface caries", one cannot wholly exclude the possible contribution of other acids, such as Propionic, to this effect. In this regard E. A. Delwicke (J. Bact. 1949, 58:395–398) reported that of 25 strains of Propionibacterium, most required Biotin for growth.

Biotin is a vitamin that is involved in the respiratory function of organisms, and appears to be required by almost all forms of life. Some organisms are able to synthesize their own, others obtain it from outside sources. It is a fortuitous circumstance that many of the microorganisms implicated in the production of dental caries require an outside source of Biotin. This creates a situation in which Biotin-depletion can be used as a tool for the inhibition of their development, and this is precisely what this invention does. By following a regimen that persistently blocks Biotin uptake, conditions can be made unfavorable for both plaque and acid formation, with resultant benefits in dental health.

Biotin-depletion or Biotin-deprivation for the caries-producing microorganisms in the mouth is brought about by the use of Dental-health Aid Products that introduce Biotin-antagonists into the mouth. There are two classes of Biotin-antagonists. The first and more numerous are the ones called "Biotin Antimetabolites".

D. W. Woolley in his book "A Study of Antimetabolites", Wiley, 1952, defines Antimetabolites as "structrual analogs antagonistic to metabolites". The structural similarity to the active Metabolites is postulated to be responsible for attachment of the Antimetabolite to sites normally receptive to the true Metabolite; this blocks the sites, and at least temporarily prevents the true Metabolite from coupling with the substrate. Coupling action with either the Metabolite or Antimetabolite is considered to be a reversible reaction, and the sites are considered to become available and then occupied over and over again. The question of which agent is most likely to attach to an available site is strictly a matter of the ratio of concentrations of Metabolites and Antimetabolites in the environment; with equal concentrations of both, equal numbers of sites are occupied by each. In order to get only 1% of the sites occupied by an active metabolite, there must be a 99 to one ratio of Antimetabolite to Metabolite concentrations.

The literature lists a substantial number of compounds that are Biotin-antimetabolites. Not all modifications of the Biotin molecule result in antagonistic properties; the compound known as Oxybiotin, for instance, in which Oxygen is substituted for the Sulfur in the molecule still retains vitamin activity in some instances.

In order to be able to visualize the modifications that are made to create Antimetabolites, the structure of the original active Biotin is shown:

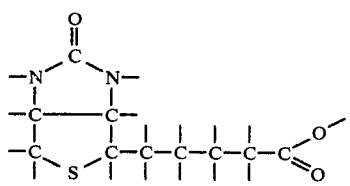

Empty valence bonds are understood to be attached to Hydrogen.

Examples of Biotin Antimetabolites are:

Desthiobiotin with 2 H substituted for S.

Biotin Sulfone with $SO_2$ substituted for S.

Ureylene Cyclohexyl Aliphatic Acids with 2 C substituted for S and derivatives with shorter side chains.

Desthio Iso Biotin substituting 2 H for S and having geometric isomerism.

Ureylene Tetrahydro Furyl Aliphatic Sulfonic Acids with O substituted for S and $SO_3H$ for COOH.

Homobiotin with addition of —$CH_2$— in the side chain.

Ureylene Cyclohexyl Valeric Acid substituting a six carbon ring for the four carbon and one sulfur 5 membered ring.

Alpha Dehydro Biotin with a double bond alpha to the COOH.

Alpha Methyl Biotin with a Methyl group on the Carbion alpha to the COOH.

Alpha Methyl Desthiobiotin with a Methyl group alpha to the COOH and 2 H in place of S.

Six Carbon-sidechain Oxybiotin with an additional C in the side-chain and substituting O for S.

Oxybiotin Sulfonic Acid substituting O for S and $SO_3H$ for COOH.

The literature also lists:
nor Biotin
bis Homobiotin
tris Homobiotin
4 Imidazole Aliphatic Acids
2 Oxo-4 Imidazolidin Caproic Acid
Thiazolidone
Benzyl Thioethers
Hydrazides and Semicarbazides of Biotin
bis Hydrazides of Suberic and Sebacic Acids
Methyl 1-3-acetyl-4-thiazolidine Carboxylate
1-2-propyl-3-acetyl-4-thiazolidine Carboxylate Methyl Ester and its Hydrazide
2-Piperidone-6-Carboxylic Acid Hydrazide
gamma (2 Carboxy-3-Indolyl) Butyric Acid Hydrazide
2-Imidazolidone-4-Carboxylic Acid Hydrazide
2-Imidazolidone-4-Caproic Acid Hydrazide
2-Imidazolidone-4-Valeric Acid Hydrazide The choice of Biotin Antimetabolite for use in this invention is not as difficult as the great number of possible Antimetabolites might imply. Compounds such as the Antibiotic Thiazolidone bring with them risks of the development of antibiotic-resistant strains of bacteria, and are to be avoided. Compounds that are very different from those encountered in living organisms can be eliminated, especially in view of the fact that ones very similar are available. Those with such minor changes as the addition of a Carbon in the side chain or unsaturation brought about by elimination of H from the side chain would be promising as candidates having low toxicity, but the most logical of all is Desthiobiotin, since it has been quite definitely established to be the Biotin precursor in some microorganisms, notably E. coli.

A very strong possibility exists that any amounts of Desthiobiotin that may be ingested by humans can be used by the intestinal microflora to manufacture Biotin, which in turn can be taken up by the human body. It has been shown that much of the Biotin supply to the body is provided by its normal intestinal microflora.

The second class of Biotin Antagonists is that of the Biotin Inactivators that combine with Biotin in such a way as to render it incapable of functioning as a vitamin.

Examples of the class of Biotin Inactivators are:

Avidin, present in the whites of eggs from avians and amphibians.

Streptavidin, produced by Streptomyces species.

An Avidin-like compound found in egg yolk. (H. W. Meslar et al, J. Biol. Chem. v 253, n 19, pp 6979–6982 (1978)), also J. C. McGuire et al, Biochem. J. 157 (2): 395–400, Aug. 1, 1976).

A Biotin-binding Protein found in chicken plasma (R. D. Mandella et al, Biochem J. 175(2) 1978 p629–634.)

Avidin is the most plentiful of the compounds of its class and having been known for the longest time, is also the best known. It is a complex Glycoprotein, having a molecular weight of 68,000. It occurs in the egg-white of chickens to the extent of 0.05%. Each molecule of Avidin has four active sites at which it can bind to Biotin. The combination formed between Avidin and Biotin is very strongly bound; the dissociation constant is $10^{-15}$ (N. M. Green, Nature, 217 (1968) p.254). The combination effectively renders Biotin incapable of acting as a vitamin.

For the purposes of this invention, one member of the class of Biotin-inactivating Biotin Antagonists of choice is Avidin.

In deciding which class of Biotin Antagonist to use for the purpose of depleting the Biotin supply available to oral microflora it is important to examine the different effects provided by each. On the one hand, a Biotin-inactivator such as Avidin, when present in sufficient amounts to react with all of the Biotin available, will completely render the Biotin unavailable to the microflora. Because of the fact that Avidin has a molecular weight of 68,000 and Biotin has a molecular weight of 244.3, and one mole of Avidin reacts with four of Biotin, the stoichometric ratio of reactants is 68,000 to $4 \times 244.3$ or 69.6 to 1. This rounds off to 70 parts by weight of Avidin to one part by weight of Biotin. So as long as there is at least 70 times as much Avidin as Biotin, the latter will be inactivated.

With a Biotin Antimetabolite in the ratio of 70 parts to one of Biotin, Biotin activity will be reduced to 1/70th of its normal value, which is unquestionably an appreciable reduction, while not a complete reduction to practically zero.

When Biotin Antagonist concentration falls off, for instance between applications, while Biotin continues to be supplied by saliva, the relative effectiveness of the Biotin Antagonist that still remains, changes, depending on its type. With Avidin, for instance, a reduction to half, that is, 35 parts of Avidin per part of Biotin, can only inactivate one half of the Biotin. A reduction of Antimetabolite from 70 parts to 35 parts per part of Biotin brings about a change from Biotin activity of 1/70th to one of 1/35th of its activity. The Biotin Antimetabolite therefore has advantages when the more ideal ratios begin to fall off.

In the examples that follow, calculations of the amounts of Biotin-antagonists to be incorporated are based on data given in the Biochemists' Handbook, Cyril Long, Editor, published by Van Nostrand in 1961. The reference shows these significant data:

Mean Flow Rate of "Resting" Saliva: 30 ml/Hr. Range: 2.5 to 110 ml/Hr.

Mean Flow Rate of Saliva Under Stimulation: 114 ml/Hr. Range: 24 to 288 ml/Hr.

Biotin Content of Saliva: about 0.8 micrograms per liter.

In order to insure effectiveness in all applications, the calculations for Biotin Antagonist concentrations that follow are all based on maxima of saliva flow rates, and consequent maximum rates of Biotin-release into the mouth. It is the ever-replenishing supply of Biotin into the oral cavity by the saliva that must be countered by the type of treatment envisioned in this invention, and in order to really be effective there should be an unflagging persistance in applied effort to block the microflora's access to the necessary Biotin. In order to make this more possible, the invention provides a variety of means for introducing Biotin- antagonists into the oral cavity. These means are Dentifrices
Mouthwashes
Chewing Gum
Confections
Tooth-coating Concentrates
Extended-release Buccal Tablets.

in order to illustrate these various means, the following examples of formulas are given.

Dentifrices

Dentifrices made according to this invention may be formulated either as tooth-pastes or tooth-powders.

Tooth-pastes have the customary ingredients such as water, abrasives, humectants, surfactants, flavorings, and may also include compounds that contribute fluoride ions or stannous ions and other items that suggest themselves to those skilled in the art, but most particularly and specifically, they comprise Biotinantagonists. Also, since such possible components as Avidin may be subject to microbial attack, it is desirable to include a preservative, or a combination of preservatives, such as Methyl and Propyl Parahydroxy Benzoates.

The rationale for Biotin-antagonist concentrations used is the following: The amount of saliva in the mouth, in the absence of stimulation, is rather surprisingly small: less than 10 ml, and more often about 4 to 6 ml. With a Biotin content of 0.8 micrograms per liter of saliva, it would mean at the most there would be 0.008 micrograms of Biotin to counteract by the toothbrushing operation. With a 70 to 1 ratio of Biotin-antagonist as a use ratio, this would call for 0.56 micrograms of Biotin-antagonist per operation. A "ribbon" of tooth-paste, as usually applied to the brush, weighs in the vicinity of one to one and a half grams. To be on the safe side, I assume that the smaller amount will be used, that is, one gram. In other words, each gram of tooth-paste should provide 0.56 micrograms of Biotin-antagonist or 56 micrograms per 100 grams.

Since the exposure to the Biotin-antagonist during toothbrushing is of such short duration, and the surfaces to be treated not all readily accessible, I prefer to provide a ten-fold excess of Biotin-antagonist concentration for assured effectiveness, that is: 560 micrograms per 100 grams of tooth-paste.

EXAMPLE 1

Tooth-paste with Biotin-inactivator type of Biotin-antagonist.

|  | Percent |
| --- | --- |
| Calcium Pyrophosphate | 40 |
| Glycerol | 20 |
| Sorbitol | 10 |
| Sodium Lauryl Sulfate | 1.5 |
| Carboxy Methyl Cellulose | 1.0 |
| Methyl Parahydroxy Benzoate | 0.2 |
| Saccharin | 0.12 |
| Propyl Parahydroxy Benzoate | 0.05 |
| Avidin | 0.00056 |
| Flavoring | to taste |
| Water | q.s. to 100 |

Avidin adsorbs onto Bentonite; such adsorption represents a first step of a reported means of isolating Avidin from egg-white (H. Fraenkel-Conrat, et al, Arch. Biochem. 39:80 1952). It is convenient and desirable to incorporate the Avidin in compositions of this invention in the form of the Avidin-Bentonite Adsorbate. In the reference cited the ratio of Avidin to Bentonite in the adsorbate is 1 to 250.

EXAMPLE 2

Tooth-paste with Avidin-Bentonite Adsorbate as Biotin-inactivator type of Biotin-antagonist.

|  | Percent |
| --- | --- |
| Calcium Pyrophosphate | 40 |
| Glycerol | 20 |
| Sorbitol | 10 |
| Sodium Lauryl Sulfate | 1.5 |
| Carboxy Methyl Cellulose | 1.0 |
| One to 250 Avidin-Bentonite Adsorbate | 0.14 |
| Methyl Parahydroxy Benzoate | 0.2 |
| Saccharin | 0.12 |
| Propyl Parahydroxy Benzoate | 0.05 |
| Flavoring | to taste |
| Water | q.s. to 100 |

EXAMPLE 3

Tooth-paste with Biotin-antimetabolite type of Biotin-antagonist.

|  | Percent |
| --- | --- |
| Calcium Pyrophosphate | 40 |
| Glycerol | 20 |
| Sorbitol | 10 |
| Sodium Lauryl Sulfate | 1.5 |
| Carboxy Methyl Cellulose | 1.0 |
| Methyl Parahydroxy Benzoate | 0.2 |
| Saccharin | 0.12 |
| Propyl Parahydroxy Benzoate | 0.05 |
| Desthiobiotin | 0.00056 |
| Flavoring | to taste |
| Water | q.s. to 100 |

EXAMPLE 4

Tooth-paste with Biotin-antimetabolite and Biotin-inactivator.

|  | Percent |
|---|---|
| Calcium Pyrophosphate | 40 |
| Glycerol | 20 |
| Sorbitol | 10 |
| Sodium Lauryl Sulfate | 1.5 |
| Carboxy Methyl Cellulose | 1.0 |
| Methyl Parahydroxy Benzoate | 0.2 |
| Saccharin | 0.12 |
| Propyl Parahydroxy Benzoate | 0.05 |
| Avidin | 0.00028 |
| Desthiobiotin | 0.00028 |
| Flavoring | to taste |
| Water | q.s. to 100 |

EXAMPLE 5

Stannous Fluoride Type Tooth-paste with alpha Methyl Biotin as Biotin-antimetabolite type of Biotin Antagonist

|  | Percent |
|---|---|
| Calcium Pyrophosphate | 40 |
| Glycerol | 20 |
| Sorbitol | 10 |
| Sodium Lauryl Sulfate | 1.5 |
| Carboxy Methyl Cellulose | 1.0 |
| Stannous Fluoride | 0.4 |
| Methyl Parahydroxy Benzoate | 0.2 |
| Saccharin | 0.12 |
| Propyl Parahydroxy Benzoate | 0.05 |
| alpha Methyl Biotin | 0.00056 |
| Flavoring | to taste |
| Water | q.s. to 100 |

EXAMPLE 6

Tooth-powder with 1:250 Avidin-Bentonite Adsorbate as Biotin-inactivator Type of Biotin Antagonist

|  | Percent |
|---|---|
| Calcium Pyrophosphate | 52 |
| Sorbitol | 40 |
| Mannitol | 2 |
| Sodium Lauryl Sulfate | 2 |
| Carboxy Methyl Cellulose | 1.43 |
| Avidin-Bentonite Adsorbate 1:250 | 0.3 |
| Stannous Fluoride | 0.40 |
| Methyl Parahydroxybenzoate | 0.20 |
| Saccharin | 0.12 |
| Propyl Parahydroxy Benzoate | 0.05 |
| Spray Dried Flavoring | 1.50 |

The preceding and following tooth-powder formaulas are calculated on the basis of the following considerations: When toothpowder is used, the amount of "charge" put on the brush is somewhat less than the amount of tooth-paste normally applied. I estimate each dose to be close to one half gram; because there may be some deviation from this figure, I use a ten-fold level of Biotin-antagonist in order to insure efficacy. Since the amount of dentifrice is one half that used in tooth-paste, the level of Biotin-antagonist in the formula has been doubled for the powder.

EXAMPLE 7

Tooth-powder with Biotin-antimetabolite Type of Biotin-antagonist.

|  | Percent |
|---|---|
| Calcium Pyrophosphate | 52 |
| Sorbitol | 40 |
| Mannitol | 2.4789 |
| Sodium Lauryl Sulfate | 2 |
| Carboxy Methyl Cellulose | 1.43 |
| Stannous Fluoride | 0.80 |
| Methyl Parahydroxy Benzoate | 0.20 |
| Saccharin | 0.12 |
| Propyl Parahydroxy Benzoate | 0.05 |
| Desthiobiotin | 0.0011 |
| Spray Dried Flavor | 1.50 |

EXAMPLE 8

Tooth-powder with Biotin-antagonists of both the Biotin-inactivating and the Biotin-antimetabolite Types.

|  | Percent |
|---|---|
| Calcium Pyrophosphate | 52 |
| Sorbitol | 40 |
| Mannitol | 2.4789 |
| Sodium Lauryl Sulfate | 2 |
| Carboxy Methyl Cellulose | 1.43 |
| Stannous Fluoride | 0.80 |
| Methyl Parahydroxy Benzoate | 0.20 |
| Saccharin | 0.12 |
| Propyl Parahydroxy Benzoate | 0.05 |
| Avidin | 0.0006 |
| Desthiobiotin | 0.0005 |
| Spray Dried Flavor | 1.50 |

Mouthwashes made according to this invention differ in purpose from most of the ones being offered today. While the implication regarding the latter seems to be that they practically eliminate microflora in the buccal cavity, in actuality, the benefits are largely esthetic. The use of mouthwashes made according to this invention are felt to be regarded as just one of a multiplicity of aids to dental health made possible by this invention, with maximum benefits available from the use of most of the aids.

The calculations for active ingredient of the mouthwashes is similar to those for tooth-pastes and tooth-powders, in that it is the Biotin in the mouth at the time of use that is to be counteracted. This is taken again as the amount in 10 ml of salivam which is more than would be normally encountered, and a ten-fold dose of Biotin-antagonist is applied. The amount of mouthwash most frequently used at a time is in the range of 15 to 30 ml. By the use of the smaller figure, there is an increase in assurance of efficacy. As in the case of dentifrices, the Biotin-antagonist dose required per use is about 0.56 micrograms; rounding off and compensating for slightly low density due to alcohol content of the solution, and multiplying by 10 for safety factor, yields a figure of a level of 40 micrograms of Biotin-antagonist per 100 grams of mouth wash.

EXAMPLE 9

Mouthwash with Biotin-antagonist of the Biotin-inactivator class.

| | Percent by wt. |
|---|---|
| S.D.Alcohol 38B | 12 |
| Glycerol | 10 |
| Sodium Lauryl Sulfate | 2 |
| Polysorbate 20 | 1 |
| Carboxy Methyl Cellulose | 0.5 |
| Methyl Parahydroxy Benzoate | 0.2 |
| Propyl Parahydroxy Benzoate | 0.05 |
| Sodium Saccharin | 0.02 |
| Avidin | 0.00004 |
| Flavoring | to taste |
| Water | q.s. 100 |

EXAMPLE 10

Mouthwash with Biotin-antagonist of the Biotin-antimetabolite class.

| | Percent by wt. |
|---|---|
| S.D.Alcohol 38B | 12 |
| Glycerol | 10 |
| Sodium Lauryl Sulfate | 2 |
| Polysorbate 20 | 1 |
| Carboxy Methyl Cellulose | 0.5 |
| Methyl Parahydroxy Benzoate | 0.2 |
| Propyl Parahydroxy Benzoate | 0.05 |
| Sodium Saccharin | 0.02 |
| Desthiobiotin | 0.00004 |
| Flavoring | to taste |
| Water | q.s. to 100 |

EXAMPLE 11

Mouthwash with Biotin-antagonists of both Inactivator and Antimetabolite classes.

| | |
|---|---|
| S.D. Alcohol 38B | 12 |
| Glycerol | 10 |
| Sodium Lauryl Sulfate | 2 |
| Polysorbate 20 | 1 |
| Carboxy Methyl Cellulose | 0.5 |
| Methyl Parahydroxy Benzoate | 0.2 |
| Propyl Parahydroxy Benzoate | 0.05 |
| Sodium Saccharin | 0.02 |
| Avidin | 0.00002 |
| alpha Dehydrobiotin | 0.00002 |
| Flavoring | to taste |
| Water | q.s. to 100 |

Any means by which Biotin Antagonists can be brought into the buccal cavity, are felt to be of benefit, as outlined in this treatise; ones that maintain significant levels of these active agents in the mouth are even more desirable. Chewing gum has characteristics that put it into the latter class.

Chewing gum has the ability of extending the release-time of its ingredients; we known this from experience with the release of sweetness and flavors. Even before actual release, Biotinantagonists in the matrix of the gum can come into contact with Biotin and react with it.

Calculations relative to optimum levels of Biotin-antagonists to be incorporated into the chewing gum have to take into account one factor not previously emphasized, and that is the element of time.

Biotin is brought into the mouth with saliva. The saliva flow is continuous, and as previously shown, has been measured at a maximum flow of 288 ml per hour under conditions of stimulation, which would be the conditions prevailing while one is chewing gum. I use a figure of 300 ml per hour for calculations, and base them on a one hour chewing period per piece of gum. After this length of time the flavor of gum is just about gone, and the gum ready to be discarded. With a Biotin content in saliva of 0.8 micrograms per liter, the 300 ml produced in an hour will have brought with it 0.24 micrograms of Biotin. With a Biotin-antagonist to Biotin ratio of 70 to one, this requires 16.8 micrograms of Antagonist. While, at the beginning of the time period involved, there will be substantial excesses of Biotin-antagonist, the situation that prevails toward the end of the hour is bound to be uncertain; for this reason I prefer to incorporate substantially double the concentration calculated, by going to 30 micrograms per piece of gum.

There are some aspects of the situation that can be looked upon as being favorable after the gum has been chewed for a while. For one thing, the sugar in the gum will have dissolved out and been swallowed. Also, the continuous washing action that takes place from this point on is bound to lower the concentrations of food residues that might ordinarily provide nourishment for bacteria; the combination of reduced Biotin availability and reduced nourishment can only be beneficial to the user.

One precaution should be observed in the making of the product when the Biotin-antagonist used is Avidin, and that relates to temperatures to which the latter is exposed. While Avidin is somewhat less sensitive to denaturation by heat than egg-white proper, it should not be subjected to temperatures in excess of 90° C., and desirably should not be added to the gum until the melt has cooled to below 60° Celsius. Where Avidin is the agent used, it may advantageously be added as Avidin-Bentonite Adsorbate previously described, since Bentonite is frequently used in chewing gums.

EXAMPLE 12

Chewing Gum with Biotin-antagonist of the Biotin-inactivator type.
Chewing gum, one stick—3 grams
Avidin—30 micrograms

EXAMPLE 13

Chewing Gum with Biotin-antagonist of the Biotin-antimetabolite type.
Chewing gum, one stick—3 grams
Desthiobiotin—30 micrograms

EXAMPLE 14

Chewing Gum with Biotin-antagonists of both Biotin-inactivator and Biotin-antimetabolite types.
Chewing gum, one stick—3 grams
Avidin—15 micrograms
alpha Methyl Desthiobiotin—15 micrograms Confections, especially those like hard candies, which take some time to dissolve in the mouth, are another form of vehicle for bringing Biotin-antagonists into the mouth, to provide the type of dental health-care aid covered in this invention.

Using a confection of the size of Life Savers as a model, I have found that each piece, weighing around 2.5 grams, takes about 10 to 12 minutes to dissolve in the mouth. The latter figure being the one that is accompanied by the larger quantity of Biotin to be released with the saliva, this is the value that the following calculations are based upon. 12 minutes are one fifth of an hour, and with a maximum output of saliva under stimulation, of 300 ml of saliva, 60 ml of saliva are released in this length of time. At 0.8 micrograms of Biotin per liter, the 60 ml of saliva release 0.048 micrograms of Biotin, which can be rounded off to 0.05 micrograms.

These 0.05 micrograms of Biotin would require 3.5 micrograms of Biotin-antagonist, according to the principle of this invention, in order to negate the microflora's possible use of the vitamin. I prefer to incorporate double this amount for more assurance of efficacy. That would be 7 micrograms of Biotin-antagonist per 2.5 gram piece of hard candy that takes 12 minutes to ingest. The percent amount comes to 280 micrograms.

Since there are so many different types of confections, it is helpful in making the calculation of Biotin-antagonist to add, to base it on the factor of time normally required to ingest a piece of the particular type of confection in question. In the previous paragraph, it was shown that a 12 minute dissolution time corresponds to a Biotin-antagonist dosage of 7 micrograms; this comes to 0.58 micrograms of Biotin antagonist per minute of time to dissolve or ingest a particular type of confection. The term "ingest" is probably more appropriate, especially in the case of chewy forms of confections.

As was mentioned in the above section on chewing gum, where the possibility exists of the Biotin-inactivator Avidin being subjected to elevated temperatures, precautions should be taken to prevent adding the Avidin at temperatures approaching 90° C.; addition should desirably be delayed until the candy melt has cooled at least to 60° C. in order to be on the safe side.

Because of the fact that the Biotin-antagonists in confections are to be ingested, I prefer to limit the representatives of the two classes of Biotin-antagonists to just two: Avidin for the Biotin-inactivating type, and Desthiobiotin for the Biotin-antimetabolite type. Avidin, as a natural component of eggs, has been ingested by humans for many centuries; Desthiobiotin as mentioned above, has been shown to be capable of acting as precursor for the biological synthesis of Biotin.

In order to include other types of confection, as examples, tests have been made to determine average consumption times on caramels weighing 9 grams each, and also on chocolate candy bars, weighing 58 grams each. The former's time of consumtion averaged close to 90 seconds each, while the latter's spread over the wide range of from 3 to about 4 minutes so the 4 minute figure is used here.

The caramels then will call for 0.87 micrograms of Biotin-antagonist per 9 grams, and the candy bars will call for 2.32 micrograms per bar, of 58 grams each.

EXAMPLE 15

Hard Candy Confection with Avidin as Biotin-inactivating Type of Biotin-antagonist.
Hard Candy Base—100 grams
Avidin—280 micrograms

EXAMPLE 16

Caramel Type of Confection with Desthiobiotin as Biotin-antimetabolite Type of Biotin-antagonist.
Caramel Base—100 grams
Desthiobiotin—10 micrograms

EXAMPLE 17

Chocolate Candy Bar with Biotin-antagonists of both Biotin-inactivator and Biotin-antimetabolite Types.
Candy Bar Base—100 grams
Desthiobiotin—2 micrograms
Avidin—2 micrograms One comment on the addition of Avidin to confections is appropriate at this point: Since confections are comestibles, it is perfectly feasible to add Avidin, where its inculsion is desired, by adding appropriate amounts of egg-white. For purposes of calculating egg-white amounts to be added, one needs only to remember that on a dry basis the egg-white contains close to 0.05% of Avidin.

The safety of using Biotin-antagonists as outlined in this specification will be discussed in a later section, and it is felt that this will show that no danger exists of interfering with the adequate provision of Biotin to the body by normal routes. Just in case anyone were to wish to make doubly sure that by ingesting unusually large quantities of Biotin-antagonist containing confections, his Biotin supply would not be diminished, it is possible to produce confections in which Biotin is supplied in an amount equivalent to that which can be negated by the antagonist in an outer layer on the confection.

Hard candies lend themselves best to this form of construction. After the body or core of the confection, containing the Biotin-antagonist has been made, the Biotin-containing coating is added. This can be accomplished by double-tabletting or pan-coating.

In the calculation for concentrations to incorporate in the confection, the dissolution time for the core of a piece of candy is first determined, the Biotin-antagonist dosage calculated by using the factor of 0.56 micrograms per minute dissolution time, and the Biotin dosage to be included in each piece's coating figured at one seventieth of the Biotin-antagonist's amount.

The variety of candy types that have been thought up are almost innumerable; the foregoing illustration has treated a type that is not intended to be chewed. The use of this invention can be extended to many that are intended to be chewed by instructing the user to hold the candy in the mouth for a short time until the Biotin-containing coating has dissolved. A convenient expedient for signalling this point would be the use of a different flavor in the coating from that of the core of the confection; when the user senses the change in flavor, he can tell that the coating has dissolved and the Biotin has been ingested. Chewing of the piece could then follow, with the assurance that the benefits of the invention would be maintained.

EXAMPLE 18

Hard Candy with Biotin-containing Coating and Biotin-antagonist of the Biotin-inactivator Type in the Core.
Hard Candy Base—100 grams
Avidin—280 micrograms
After tablets have been formed, they are placed in pan-coater and the following formulation applied:
Sugar—5 grams
Water—5 grams
Biotin—4 micrograms

EXAMPLE 19

Hard Candy with Biotin-containing Coating and Biotin-antagonist of the Biotin-antimetabolite Type in the Core.
Hard Candy Base—100 grams
Desthiobiotin—280 micrograms After the tablets have been formed, they are placed in a pan-coater and the following solution is applied:
Sugar—5 grams
Water—5 grams
Biotin—4 micrograms

EXAMPLE 20

Hard Candy with Biotin-containing Coating an Biotin-antagonists of both Biotin-antimetabolite and Biotin-inactivator Type in the Core.
Hard Candy Base—100 grams
Desthiobiotin—140 micrograms
Avidin—140 micrograms After the tablets are formed, they are placed in a pan-coater and the following solution is applied:
Sugar—5 grams
Water—5 grams
Biotin—4 micrograms Another means of applying the principle of this invention is represented by a tooth-coating concentrate, whose description here follows. It is a solution intended to be applied to the teeth at times between meals, and it contains an appreciably higher concentration of Biotin-antagonist than does mouthwash. It also differs from mouthwash in not being intended to be rinsed away after use. The concentrate is desirably made as bland as possible in taste, in order not to stimulate saliva production, since this would also bring additional Biotin to the scene. The concentrate is meant to remain on the tooth surfaces where its Biotin-antagonist content can be most effective in blocking Biotin-uptake by caries producer type of microorganisms.

The concentration of Biotin-antagonist in the concentrate is based on the length of time that it is expected to remain effective. The calculations that follow are based on a one-hour duration. Longer periods are burdened by increased uncertainties that arise from such effects as swallowing, speaking, smoking and any other activity that might serve to displace the coating from the teeth.

In the absence of stimulation the maximum saliva production rate in the reference previously cited is given at 110 ml per hour. The amount of Biotin in 110 ml therefore is the maximum that must be negated by one treatment, and at a concentration of 0.8 micrograms per liter of saliva, this comes to 0.088 micrograms of Biotin. In the 70 to 1 ratio of Biotin-antagonist, this calls for a dosage of 6.16 micrograms of the latter. 10 micrograms will provide some overage, and yields a convenient factor for calculations.

By using either a swab or a spray, an amount of ½ ml is adequate for supplying a coating for the teeth. With a charge of 10 micrograms per ½ ml, the percent figure of Biotin-antagonist in the concentrate comes to 2000 micrograms, or more conveniently put, 2 milligrams. In order to minimize the danger of a person's taking excessive quantities of this concentrate, it is convenient to package it in 5 ml vials, provided with restricted openings, much like the product known as Binaca, which is sold as a breath-freshener.

It may reasonably be expected that the tooth surfaces that are contacted by the tongue will be washed free of concentrate soon after the latter is applied. This is not of too much concern; very few cavities ever develop on these surfaces. The critical areas are those at which quiescent conditions prevail: in crevices, between teeth, at the gum-line; in other words where deposits remain physically more or less "hidden" and undisturbed.

EXAMPLE 21

Tooth-coating Concentrate with Biotin-antimetabolite Type of Biotin-antagonist.

|  | Percent |
| --- | --- |
| Glycerine | 30 |
| Carboxy Methyl Cellulose | 2 |
| Bentonite | 2 |
| Methyl Parahydroxy Benzoate | 0.2 |
| Propyl Parahydroxy Benzoate | 0.05 |
| Desthiobiotin | 0.002 |
| Flavoring | to taste |
| Water | q.s. to 100 |

The Avidin-Bentonite Adsorbate previously mentioned can be advantageously used in this application; it saves the extra step of separating the Avidin in the purification of the latter.

EXAMPLE 22

Tooth-coating Concentrate with Biotin-antagonist of the Biotin-inactivator Type.

|  | Percent |
| --- | --- |
| Glycerine | 30 |
| Carboxy Methyl Cellulose | 2 |
| Avidin-Bentonite Adsorbate 1:250 | 0.5 |
| Bentonite | 1.5 |
| Methyl Parahydroxy Benzoate | 0.2 |
| Propyl Parahydroxy Benzoate | 0.05 |
| Flavoring | to taste |
| Water | q.s. to 100 |

Other ingredients may be incorporated in this concentrate, as will be self-evident to those skilled in the art, such as surface-active agents, viscosity controlling agents and additives to add to the esthetic appeal, without departing from the scope of the invention. Levels of Biotin-antagonists may also be varied to provide action for different periods of duration, or to vary the overages. Other Biotin-antagonists may be incorporated, as may mixtures of these.

The following example illustrates a formula that makes use of a mixture of Biotin-antagonists.

EXAMPLE 23

Tooth-coating Concentrate with Biotin-antagonists of both the Class of Biotin-antimetabolites and the Class of Biotin-inactivators.

|  | Percent |
| --- | --- |
| Glycerine | 30 |
| Carboxy Methyl Cellulose | 2 |
| Bentonite | 2 |
| Methyl Parahydroxy Benzoate | 0.2 |
| Propyl Parahydroxy Benzoate | 0.05 |
| Desthiobiotin | 0.001 |
| Avidin | 0.001 |
| Water | q.s. to 100 |

One more means whereby the microflora of the mouth can be deprived of their supply of Biotin is represented by Extended-release Buccal Tablets containing Biotin-antagonist. By placing tablets of this description in the mouth, a steady supply of Biotin-negating substance or substances can be provided over an extended period of time. Their use is especially recommended for times when one is resting, and the example that will be described in detail refers to an 8-hour tablet, since this is widely accepted as a normal night's sleep.

Basic data upon which calculations are made are:
Saliva production without stimulation: 110 ml/hour max.
Biotin content of saliva: 0.8 micrograms per liter
Effective Biotin-antagonist to Biotin ratio: 70:1
Desired period of effectiveness: 8 hours.

There are two basic types of extended release tablets. In one there is a substantially insoluble matrix, from which an active principle is leached out over a period of time. In the other, the whole tablet dissolves at a slow rate, with the excipient and the active ingredient being released together. I prefer the latter for use with this invention. U.S. Pat. Nos. 3,039,933 and 3,362,881 describe the production of this type of tablet.

There is a property that is common to both types of tablets: while they provide a prolonged release time for the active ingredient, they definitely do not provide constant release rates. In the stable-matrix type, the reservoir of active ingredient becomes gradually more dilute. In the dissolving type, the size of the tablet diminishes with time, and as the surface area decreases so does the rate of dissolution. In both cases this results in a gradual fall-off of the rate of release of the active ingredient. In some cases this behavior is desirable, as with drugs in which a certain level of active ingredient is to be established, and then only maintenance levels are desired, which are much lower. In this invention, this situation is not desired and requires countermeasures.

In order to visualize the action that takes place during the dissolution of tablets such as these, let us consider an 8-hour release tablet that is to counter the Biotin brought into the mouth with the saliva. At 110 ml per hour and 0.8 micrograms per liter of Biotin, the 880 ml maximum released would bring along 0.704 micrograms of Biotin. With the 1 to 70 factor previously described for the Biotin-antagonist value, it would appear that one should incorporate 49.3 micrograms for release over the 8 hour period. However, in order to have released this quantity, at a constantly decreasing rate of release, the average rate would only prevail at the mid-point in time, with a double rate in the first half period and a half rate in the second half of the period.

At first thought, it might appear that to overcome this situation, one should double the dosage in the tablet, but this is only a partial answer: the tablet is just as much gone toward the end of the time period and the release rate is too low as the period nears its end, unless great excesses of active ingredient had been added.

This problem is overcome in this invention by the use of a 16-hour duration tablet that starts out with a double dose of Biotin-antagonist. In this way, the tablet's midrate of release is just reached at the 8-hour juncture; release rates before this will be higher than actually needed, but protection is provided at all times. The tablet then would contain 98.6 micrograms of Biotin-antagonist, and be designed for a 16 hour duration, but only used for 8. Actually, the dosage is best divided up among two tablets, one to be placed next to each cheek at bedtime.

It is to be noted that extended-release tablets of this type for use in this invention, can also be made for other periods of duration, for use for example between meals. The calculation for dosage is two times the amount required to counteract the quantity of Biotin releasable in the period one wishes to cover, and the tablet should be dissolvable in twice this period.

It is to be understood that I do not limit my invention in regard to the tablet form used to carry the Biotin-antagonist. Desirably, the tablet base is of the class of materials such as Carboxy Methyl Cellulose, Polyacrylic Acid and similar substances that do not readily provide nourishment for microorganisms; natural gums often serve as food for bacteria and molds and are less advantageous. Nor do I intended to limit the scope of the invention to the particular 16-hour release tablet described; a multiple-layered tablet with a very high inner concentration of Biotin-antagonist and successively lower levels in the outer layers can provide a release rate that is more constant, but the increased cost of a more complicated tablet has to be weighed against the cost of using somewhat more Biotin-antimetabolite to retain efficacy, in a more simply made tablet.

EXAMPLE 24

Extended-release Buccal Tablets for 8-hour Effectiveness with Biotin-inactivating Type of Biotin-antagonist.
Extended-release Tablet Base—100 grams
Avidin—4.93 mg
Compress to yield 16-hour durability tablets of 1 gram each.
Two tablets to be placed in mouth at bedtime, one next to each cheek.

EXAMPLE 25

Extended-release Buccal Tablets for 4-hour Between-meal Use with Biotin-antimetabolite Type of Biotin-antagonist.
Extended-release Tablet Base—100 grams
Desthiobiotin—2.97 mg
Compress to yield 8-hour durability tablets of 1 gram each.
Two tablets to be placed in mouth between meals, one next to each cheek.

EXAMPLE 26

Extended-release Buccal Tablet for 8-hour Effectiveness with Biotin-antagonists of both the Biotin-inactivator Type and the Biotin-antimetabolite Type.
Extended-release Tablet Base—100 grams
Avidin—2.97 mg
Desthiobiotin—2.97 mg
Compress to yield 16-hour durability tablets of one gram each.
Two tablets to be placed in mouth at bedtime, one next to each cheek.

Considerations Regarding Possible Health Hazards From the Use of this Invention.

Since Biotin is an essential Vitamin for Humans, it is necessary to examine the possible effects on man's supply and reserves, that might be brought about by the maximum use of the features of this invention.

These are the significant factors that make up the whole picture:

1. The treatments are aimed at the Biotin that is in the mouth only. They are not directed at the body's supply of Biotin to reduce levels in the mouth. The magnitudes of Biotin to be negated and the magnitudes of the agents used involve an ecosystem represented by less than 10 ml of saliva at any time, and a total day's production that is given at a maximum of 1500 ml by both the Biochemists' Handbook (Van Nostrand, 1962) and the Textbook of Biochemistry by West & Todd (MacMillan, 1952). The former reference gives the Biotin content of saliva at 0.8 micrograms per liter. Even at a maximum of 2 liters of saliva, the total Biotin that might be negated comes to only 1.6 micrograms per day.

The antagonists, even with 100% overages could negate a maximum of only 3.2 micrograms of Biotin per day.

2. The human body, representing a much larger system, receives Biotin supplies from 2 sources (Recommended Dietary Allowances, publ. by NAS, 1974):

a. from food: 100 to 300 micrograms per day.

b. from normal intestinal microflora in amounts sufficient to show levels 3 to 6 times the amount from the food to be discarded as surplus in the urine. Even using these factors on the smaller figure of Biotin from food yields figures of 300 to 600 micrograms that the body has above its needs. Comparing these data showing (1) the amounts of Biotin possibly negated by the use of this invention: slightly over 3 micrograms, with (2) Biotin surpluses of from 300 to 600 micrograms, one can reasonably say that the danger that Biotin shortages might occur, is extremely unlikely. Other facts that support the impression of confidence in the maintenance of adequate Biotin supplies for the body. For one, the NAS has set up no RDA's for Biotin because of the ample supplies of this vitamin in our diets. In an experiment by Sydenstricker (JAMA, 1942, 118: 1199–1200) it was shown to be necessary to feed human subjects a diet consisting of 30% of egg-white for seven weeks before observing acute symptoms of Biotin deficiency; the dosage of Avidin was massive: enough to be capable of inactivating Biotin in the order of 900 micrograms per day.

The possibility of depriving the body of less than 4 micrograms of Biotin per day hardly seems likely to evoke similar effects by the use of this invention.

I claim:

1. Dental Health-care Aids compositions selected from the group consisting of dentifrice toothpastes dentifrice toothpowders mouthwashes chewing gums confections tooth-coating concentrates and extended-release buccal tablets comprising effective amounts optimum for a biotin-uptake blocking regimen unfavorable for biotin-requiring micro-organisms implicated in the human mouth mini-ecosystem production of dental caries plaque, and acid formation, in the mouth of Biotin-antagonists.

2. The features of claim 1, wherein the Dental Health-care Aid is a dentifrice.

3. The features of claim 1, wherein the Dental Health-care Aid is a dentifrice of the tooth-paste type.

4. The features of claim 1, wherein the Dental Health-care Aid is a dentifrice of the tooth-powder type.

5. The features of claim 1, wherein the Dental Health-care Aid is in the form of mouthwash.

6. The features of claim 1, wherein the Dental Health-care Aid is in the form of chewing gum.

7. The features of claim 1, wherein the Dental Health-care Aid is in the form of confections.

8. The features of claim 1, wherein the Dental Health-care Aid is in the form of confections having a Biotin-containing outer layer.

9. The features of claim 1, wherein the Dental Health-care Aid is a concentrate for coating teeth.

10. The features of claim 1, wherein the Dental Health-care Aid is in the form of extended-release buccal tablets.

11. Dental Health-care Aids compositions selected from the group consisting of dentifrice toothpastes dentifrice toothpowders mouthwashes chewing gums confections tooth-coating concentrates and extended-release buccal tablets comprising effective amounts optimum for a biotin-uptake blocking regimen unfavorable for biotin-requiring micro-organisms implicated in the human mouth mini-ecosystem production of dental caries plaque, and acid formation, in the mouth of Biotin-antagonists of the Biotin-inactivator Type.

12. The features of claim 11, wherein the Dental Health-care Aid is a dentifrice.

13. The features of claim 11, wherein the Dental Health-care Aid is a dentifrice of the tooth-paste type.

14. The features of claim 11, wherein the Dental Health-care Aid is a dentifrice of the tooth-powder type.

15. The features of claim 11, wherein the Dental Health-care Aid is in the form of a mouthwash.

16. The features of claim 11, wherein the Dental Health-care Aid is in the form of chewing gum.

17. The features of claim 11, wherein the Dental Health-care Aid is in the form of confections.

18. The features of claim 11, wherein the Dental Health-care Aid is in the form of confections having a Biotin-containing outer layer.

19. The features of claim 11, wherein the Dental Health-care Aid is a concentrate for coating teeth.

20. The features of claim 11, wherein the Dental Health-care Aid is in the form of extended-release buccal tablets.

21. Dental Health-care Aids compositions selected from the group consisting of dentifrice toothpastes dentifrice toothpowders mouthwashes chewing gums confections tooth-coating concentrates and extended-release buccal tablets comprising effective amounts optimum for a biotin-uptake blocking regimen unfavorable for biotin-requiring micro-organisms implicated in the human mouth mini-ecosystem production of dental caries plaque, and acid formation, in the mouth of Biotin-antagonists of the Biotin-antimetabolite type.

22. The features of claim 21, wherein the Dental Health-care Aid is a dentifrice.

23. The features of claim 21, wherein the Dental Health-care Aid is a dentifrice of the tooth-paste type.

24. The features of claim 21, wherein the Dental Health-care Aid is a dentifrice of the tooth-powder type.

25. The features of claim 21, wherein the Dental Health-care Aid is in the form of mouthwash.

26. The features of claim 21, wherein the Dental Health-care Aid is in the form of chewing gum.

27. The features of claim 21, wherein the Dental Health-care Aid is in the form of confections.

28. The features of claim 21, wherein the Dental Health-care Aid is in the form of confections having a Biotin-containing outer layer.

29. The features of claim 21, wherein the Dental Health-care Aid is in the form of a concentrate for coating teeth.

30. The features of claim 21, wherein the Dental Health-care Aid is in the form of extended-release buccal tablets.

31. Dental Health-care Aids compositions selected from the group consisting of dentifrice toothpastes dentifrice toothpowders mouthwashes chewing gums confections tooth-coating concentrates and extended-release buccal tablets comprising effective amounts optimum for a biotin-uptake blocking regimen unfavorable for biotin-requiring micro-organisms implicated in the human mouth mini-ecosystem production of dental caries plaque, and acid formation, in the mouth of Biotin-antagonists of both the Biotin-inactivator type and the Biotin-antimetabolite type.

32. The features of claim 31, wherein the Dental Health-care Aid is a dentifrice.

33. The features of claim 31, wherein the Dental Health-care Aid is a dentifrice of the tooth-paste type.

34. The features of claim 31, wherein the Dental Health-care Aid is a dentifrice of the tooth-powder type.

35. The features of claim 31, wherein the Dental Health-care Aid is in the form of mouthwash.

36. The features of claim 31, wherein the Dental Health-care Aid is in the form of chewing gum.

37. The features of claim 31, wherein the Dental Health-care Aid is in the form of confections.

38. The features of claim 31, wherein the Dental Health-care Aid is in the form of confections having a Biotin-containing outer layer.

39. The features of claim 31, wherein the Dental Health-care Aid is in the form of a concentrate for coating teeth.

40. The features of claim 31, wherein the Dental Health-care Aid is in the form of extended-release buccal tablets.

* * * * *